(12) United States Patent
Justin et al.

(10) Patent No.: US 7,112,204 B2
(45) Date of Patent: Sep. 26, 2006

(54) TIBIAL TUBERCLE OSTEOTOMY FOR TOTAL KNEE ARTHROPLASTY AND INSTRUMENTS AND IMPLANTS THEREFOR

(75) Inventors: Daniel F. Justin, Logan, UT (US); E. Marlowe Goble, Alta, WY (US)

(73) Assignee: MedicineLodge, Inc., Logan, UT (US)

( * ) Notice: Subject to any disclaimer, the term of this patent is extended or adjusted under 35 U.S.C. 154(b) by 571 days.

(21) Appl. No.: 10/360,250

(22) Filed: Feb. 6, 2003

(65) Prior Publication Data
US 2004/0158255 A1    Aug. 12, 2004

(51) Int. Cl.
*A61F 5/00*     (2006.01)
*A61B 17/00*    (2006.01)

(52) U.S. Cl. ........................................................ 606/87

(58) Field of Classification Search ................... 606/79, 606/83–89, 167, 175, 120, 170, 174, 182, 606/183, 206; 132/75.4–75.6, 76.4; 30/26–29
See application file for complete search history.

(56) References Cited

U.S. PATENT DOCUMENTS

| | | | |
|---|---|---|---|
| 487,068 A * | 11/1892 | Drinkwater et al. ........ 606/126 |
| 3,835,860 A | 9/1974 | Garretson |
| 4,180,909 A * | 1/1980 | Lind .......................... 30/332 |
| 4,201,213 A | 5/1980 | Townsend |
| 4,208,792 A | 6/1980 | Ewig, Jr. |
| 4,733,663 A | 3/1988 | Farley |
| 4,777,948 A | 10/1988 | Wright |
| 5,019,081 A | 5/1991 | Watanabe |
| 5,026,375 A | 6/1991 | Linovitz et al. |
| 5,112,334 A | 5/1992 | Alchermes et al. |
| 5,470,328 A | 11/1995 | Furnish et al. |
| 5,582,618 A | 12/1996 | Chin et al. |
| 5,617,633 A * | 4/1997 | Lee .............................. 30/28 |
| 5,649,947 A | 7/1997 | Auerbach et al. |
| 5,716,405 A | 2/1998 | Mittelman |
| 5,766,177 A | 6/1998 | Lucas-Dean et al. |
| 5,851,214 A | 12/1998 | Larsen et al. |
| 5,873,886 A | 2/1999 | Larsen et al. |
| 5,911,724 A | 6/1999 | Wehrli |
| 6,200,320 B1 | 3/2001 | Michelson |
| 2003/0135217 A1 | 7/2003 | Buttermann et al. |

FOREIGN PATENT DOCUMENTS

| | | |
|---|---|---|
| EP | 0 378 433 B1 | 5/1995 |
| WO | WO 02/45599 A1 | 6/2002 |
| WO | WO 02/089681 A1 | 11/2002 |

* cited by examiner

*Primary Examiner*—Eduardo C. Robert
*Assistant Examiner*—Michael J. Araj
(74) *Attorney, Agent, or Firm*—Workman Nydegger

(57) ABSTRACT

A method of performing a tibial tubercle osteotomy includes cutting a bone portion of a tibial tubercle from a remaining portion of the tibial tubercle, at least a portion of a patella ligament being attached to the bone portion. The bone portion of the tibial tubercle is separated from the remaining portion of the tibial tubercle such that the patella ligament remains attached to the bone portion. After completing a surgical procedure, the separated bone portion of the tibial tubercle is reattached to the remaining portion of the tibial tubercle.

19 Claims, 7 Drawing Sheets

TIBIAL TUBERCLE OSTEOTOMY FOR TOTAL KNEE ARTHROPLASTY AND INSTRUMENTS AND IMPLANTS THEREFOR

CROSS-REFERENCE TO RELATED APPLICATIONS

Not applicable.

BACKGROUND OF THE INVENTION

1. The Field of the Invention

The present invention relates to methods and corresponding instruments for gaining surgical access to the knee cavity by performing a tibial tubercle osteotomy as part of a minimally invasive total or partial knee arthroplasty or other knee related surgery.

2. Related Technology

As a result of accident, deterioration, or other causes, it is often necessary to surgically replace all or portions of a knee joint. Joint replacement is referred to as arthroplasty. Conventional total knee arthroplasty requires a relatively long incision that typically extends longitudinally along the lateral side of the leg spanning across the knee joint. To allow the use of conventional techniques, instruments, and implants, the incision typically extends proximal of the knee and into the muscular tissue. In general, the longer the incision and the more muscular tissue that is cut, the longer it takes for the patient to recover and the greater the potential for infection.

Accordingly, what is needed are minimally invasive procedures and corresponding apparatus for accessing the knee joint to perform total or partial knee arthroplasty.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
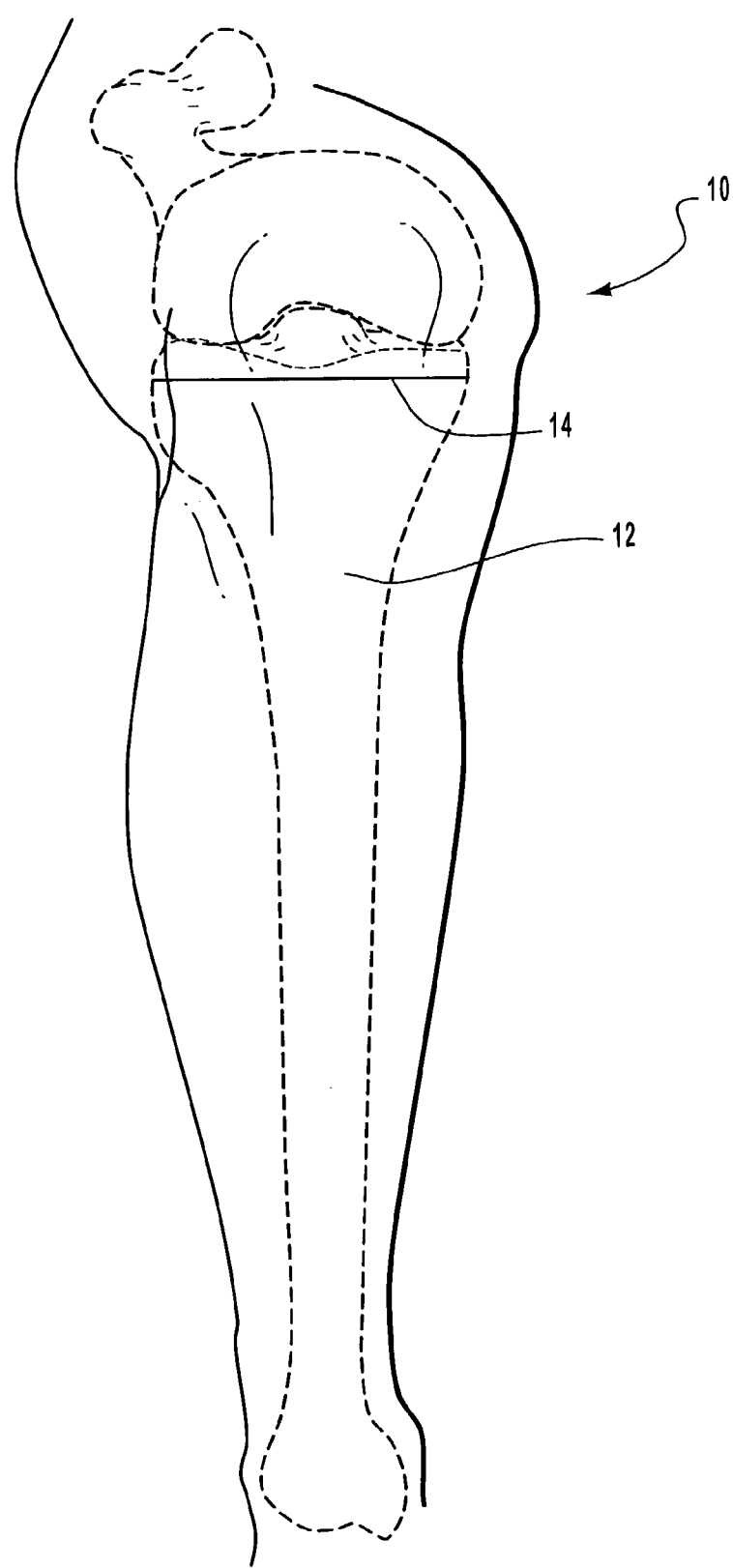
FIG. 1 is an elevated front view of a leg in a bent position.
Figure 2:
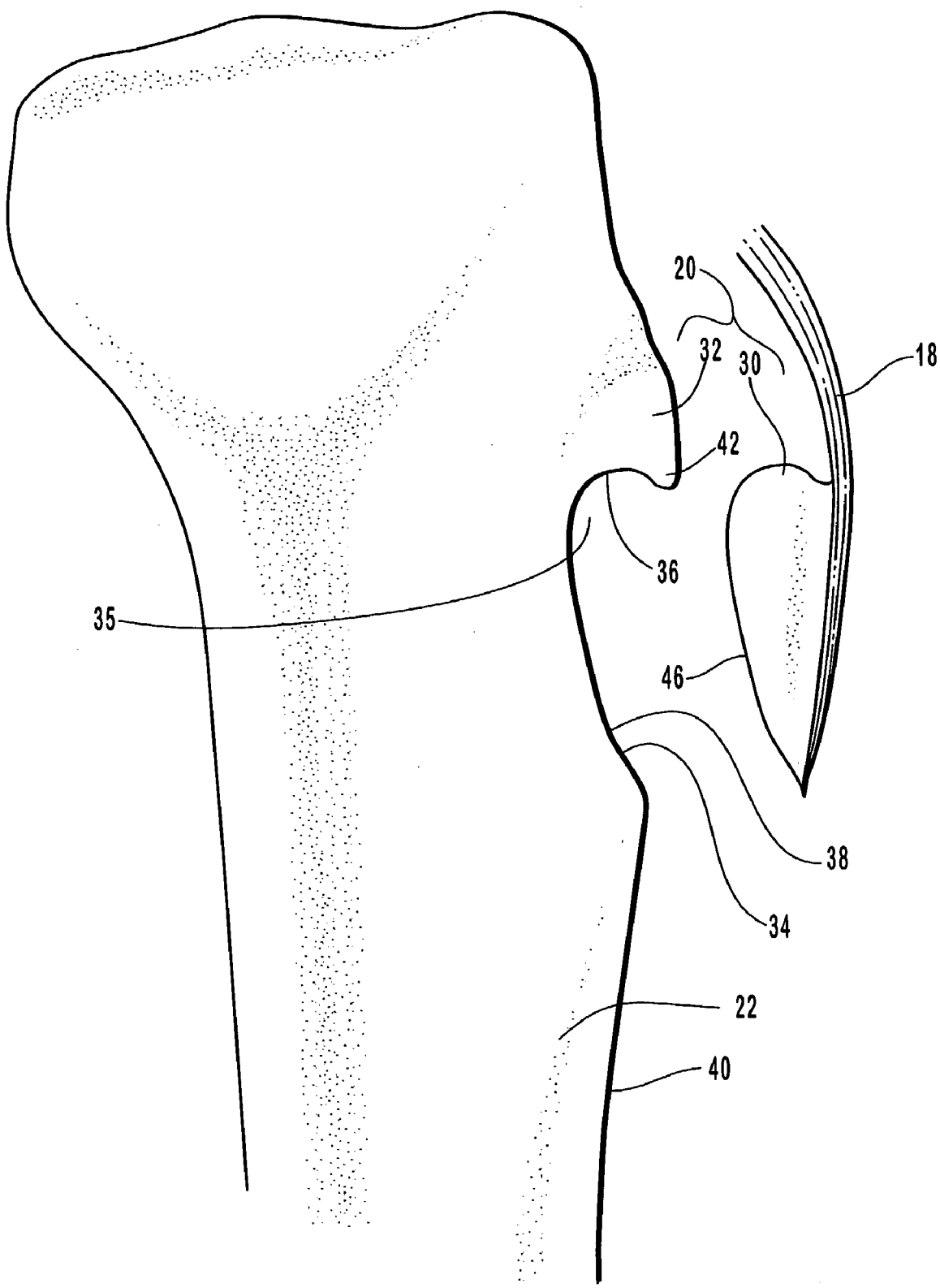
FIG. 2 is a elevated front view of a tibia of the leg shown in FIG. 1 with a portion of the tibial tuberosity removed.

The present invention relates to methods and corresponding instruments for performing a tibial tubercle osteotomy to gain access to the knee cavity as part of a minimally invasive total or partial knee arthroplasty or other knee related surgery. By way of example and not by limitation, depicted in FIG. 1 is a knee 10 having an anterior side 12. Knee 10 is flexed to about 90 degrees. A transverse incision 14, approximately 10 cm long, is made mediolaterally through the skin layer across the midline of knee 10 proximal of the tibial tuberosity. As depicted in FIG. 2, the tissue is retracted exposing in part a patellar ligament 18 and a tibial tuberosity 20 of a tibia 22. A portion of tibial tuberosity 20 connected to patellar ligament 18 is now elevated such that patellar ligament 18 remains connected thereto.

Specifically. FIG. 2 shows a lateral view of the proximal cad of tibia 22 A distal portion 30 of tibial tuberosity 20 has been elevated while a proximal portion 32 of tibial tuberosity 20 remains integral with tibia 22. Patellar ligament 18 is excised from proximal portion 32 of tibial tuberosity 20 so tat the distal end of patellar ligament 18 can be freely elevated in connection with distal portion 30 of tibial tuberosity 20. Tn one embodiment, distal portion 30 of tibial tuberosity 20 is sized such that between about ⅓ to about ½ of the central mediolateral width of patellar ligament 18 and tibial tuberosity 20 are osteotimized from the proximal end of tibia 22. Thus about ⅓ to about ½ of the distal contact surface of patellar ligament 18 remains connected to distal portion 30 of tibial tuberosity 20.

Tibia 22 has an anterior cut surface 34. With reference to the lateral side view of tibia 22 depicted in FIG. 2, cut surface 34 includes a proximally arched undercut portion 36 formed on the distal end of proximal portion 32 of tibial tuberosity 20. As a result of cut surface 34, proximal portion 32 of tibial tuberosity 20 terminates at a distally projecting anterior ridge 42.

Cut surface 34 also includes a distally sloping portion 38 extending from undercut portion 36 to an anterior border 40 of tibia 22. Cut surface 34 partially bounds a pocket 35 and has a transverse configuration taken along a plane extending proximal to distal that is similar to a vertically bisected heart design as depicted on conventional playing cards. In contrast to forming a smooth bisected heart shape design, cut surface 34 can also form a sharp or slightly rounded inside angle that is typically 90° or less.

Figure 3:
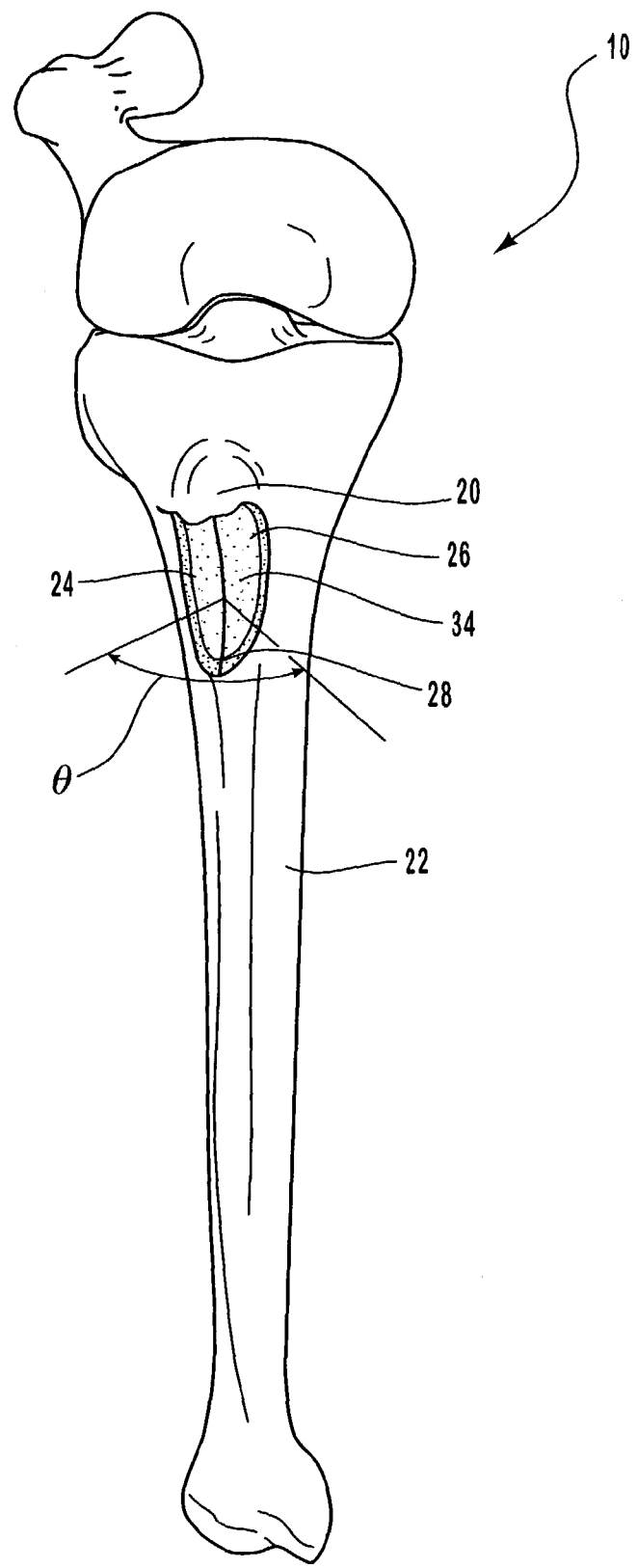
FIG. 3 is an elevated side view of the tibia shown in FIG. 2.

As depicted in FIG. 3, cut surface 34 also has a substantially wedged shaped transverse configuration taken along a plane extending anterior to posterior. Specifically, cut surface 34 comprises a lateral side 24 and an opposing medial side 26 that each slope inwardly so as to intersect at a vertical midline 28. In one embodiment, the inside angle θ between lateral side 24 and medial side 26 is in a range between about 60° to about 120° with about 80° to about 100° being more preferred. In alternative embodiments, cut surface 34 can be substantially flat extending mediolaterally or can form a rounded groove.

Elevated distal portion 30 of tibial tuberosity 20 has a cut surface 46 that is complementary to cut surface 34. As will be discussed below in greater detail, one of the benefits of the configuration of cut surfaces 34 and 46 is that once the procedure is complete, distal portion 30 of tibial tuberosity 20 is easily reinserted within pocket 35. The complementary mating with undercut surface 36 helps lock distal portion 30 within pocket 35 as distal potion 30 is pulled proximal by patellar ligament 18.

Figure 4:
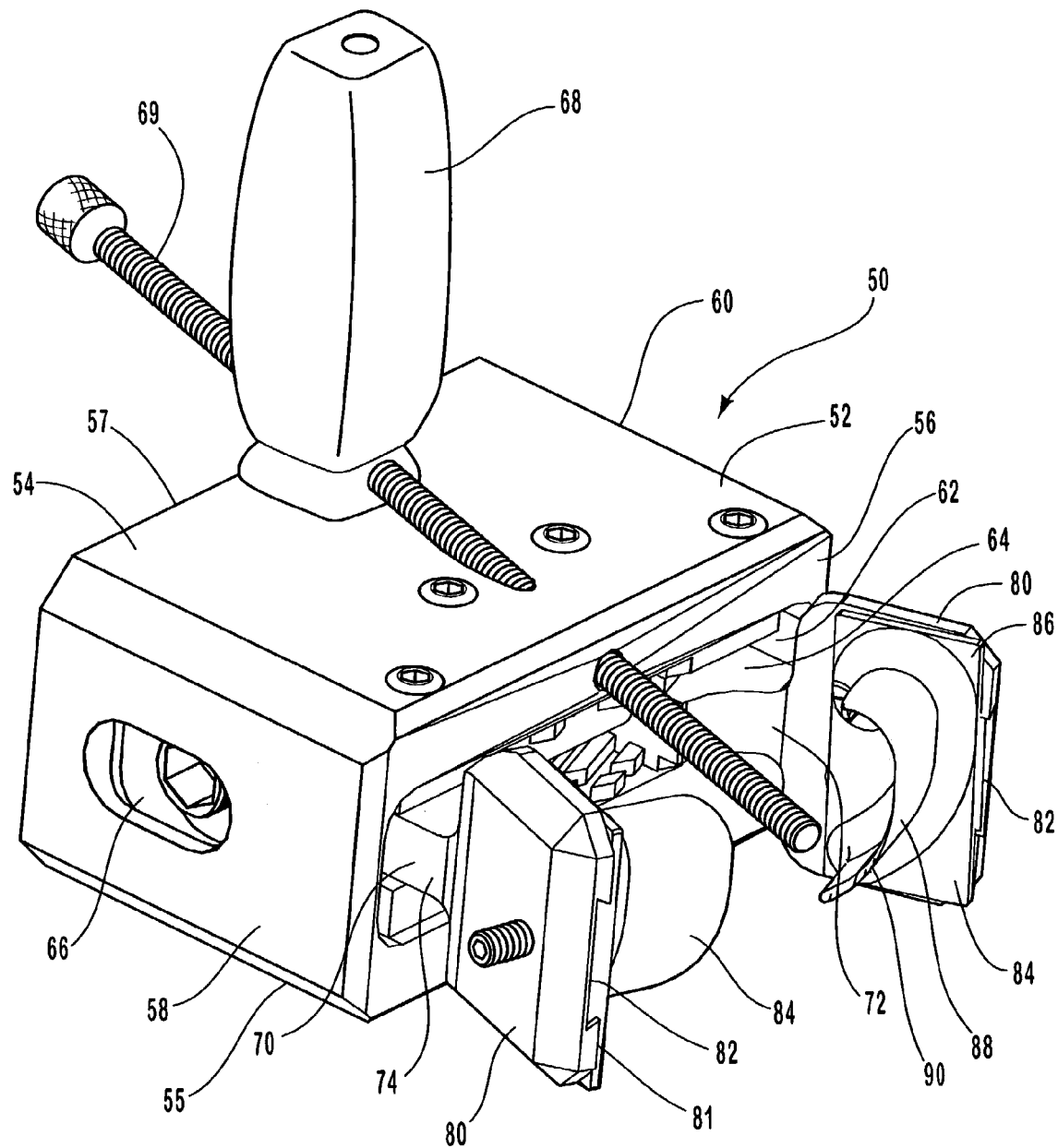
FIG. 4 is a perspective view of a die cutter.

Distal portion 30 of tibial tuberosity 20 can be elevated using a number of different techniques. By way of example and not by limitation, depicted in FIG. 4 is one embodiment of a die cutter 50 incorporating features of the present invention. Die cutter 50 comprises a housing 52 having a substantially box shaped configuration. Housing 52 has a front face 56 and an opposing back face 57 with side faces 58 and 60 extending therebetween. A top face 54 and an opposing bottom face 55 also extend between faces 56 and 57. Housing 52 bounds a chamber 62. Chamber 62 communicates with the exterior through an elongated slot 64 formed on front face 52 and an opening 66 formed on each side face 58 and 60.

A handle 68 outwardly projects from top face 54 of housing 52. A threaded alignment bolt 69 passes through handle 68 and a portion of housing 52 so as to centrally project beyond front face 56 of housing 52. Alignment bolt 69 threadedly engages with handle 68 and/or housing 52 such that selective rotation of alignment bolt 69 facilitates selective positioning of alignment bolt 69 beyond front face 56 of housing 52.

Figure 5:
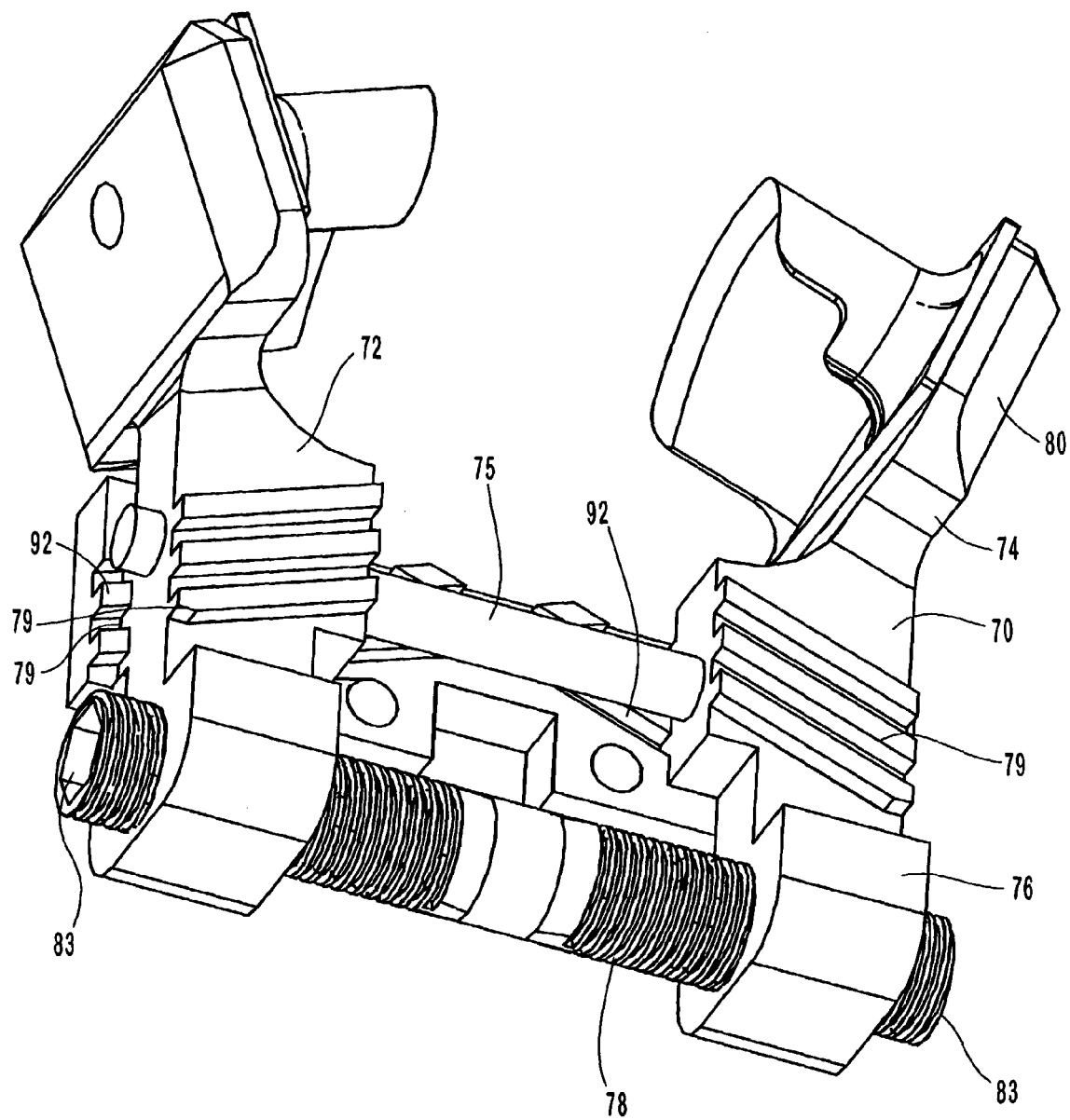
FIG. 5 is a perspective view of the arm assembly of the die cutter shown in FIG. 4.

Partially disposed within chamber 62 of housing 52 are a pair of translating arms 70 and 72. As depicted in FIG. 5, each translating arm 70 and 72 has a distal end 74 and an opposing proximal end 76. In one embodiment of the present invention, means are provided for selectively advancing at least one of the first and second translating arms 70, 72 toward the other. By way of example and not by limitation, a shaft 78 has threads formed along each end thereof with the threads being oriented in opposing directions. Each translating arm 70 and 72 is threaded onto a corresponding end of shaft 78. Accordingly, selective rotation of shaft 78 causes translating arms 70, 72 to either move together or move apart. A socket 83 is formed on each end face of shaft 78. Shaft 78 is selectively rotated by inserting a tool, such as a drill bit, through one of openings 66 (FIG. 4) of housing 52 and into socket 83 of shaft 78. Rotation of the tool thus facilitates rotation of shaft 78.

In alternative embodiments for the means for selectively advancing, it is appreciated that shaft 78 can be replaced with a variety of other conventional threaded shaft or bolt mechanisms. Furthermore, shaft 78 can be replaced with elongated levered handles or other conventional apparatus that facilitate manual movement of translating arms 70 and 72. In yet other embodiments, it is appreciated that hydraulic, pneumatic, or electrical mechanisms can be used for movement of translating arms 70 and 72.

A plurality of spaced apart rails 79 outwardly project from each side of each translating arm 70, 72. Rails 79 mesh with complementary rails 92 formed on the interior of housing 52. The meshing of rails 79 and 92 helps to ensure that translating arms 70, 72 are maintained in alignment during movement. Proper alignment of translating arms 70, 72 is further maintained by a pin 75 slidably extending through each of translating arms 70, 72.

Returning to FIG. 4, distal end 74 of each translating arm 70, 72 extends outside of chamber 62 through slot 64. Mounted at distal end 74 of each translating arm 70 and 72 is an outwardly sloping head plate 80. Each head plate 80 has an interior face 81 with an undercut engagement slot 82 formed thereon. Each interior face 81 is disposed in a corresponding plane. The planes intersect so as to form an inside angle that is substantially equal to the angle θ formed on cut surface 34. Slidably disposed within each slot 82 is a die 84. Each die 84 has a base 86 that is connected with a corresponding head plate 80 by being slidably engaged within slot 82. As a result, dies 84 can be easily replaced with new dies or with dies having an alternative configuration.

A blade 88 outwardly projects from each base 86 so as to extend orthogonally from interior face 81 of the corresponding head plate 80. Each blade 88 terminates at a free sharpened edge 90. Each blade 88 and corresponding sharpened edge 90 has a profile that is the same configuration as the profile of cut surface 34 of tibial tuberosity 20 previously discussed. Blades 88 are disposed so as to opposingly face at an intersecting angle. Accordingly, as shaft 78 is selectively rotated, translating arms 70, 72 move together causing sharpened edges 90 to mate together.

During use, once tibial tuberosity 20 is exposed as discussed above, die cutter 50 is positioned such that dies 84 are positioned on the lateral and medial side of tibial tuberosity 20. The free end of bolt 69 rests against the anterior surface of tibial tuberosity 20 and helps to facilitate proper positioning of dies 84. In this regard, bolt 69 functions as a spacer. In alternative embodiments, bolt 69 can be replace with a variety of other mechanism that permit selective spacing adjustment. For example, a rod and clamp configuration can be used.

Once die cutter 50 is appropriately positioned, shaft 78 is selectively rotated, such as by the use of a drill, so that translating arm 70 and 72 are advanced together. In so doing, the dies 84 penetrate laterally and medially into tibial tuberosity 20. Dies 84 continue to advanced until distal portion 30 of tibial tuberosity 20 is separated from proximal portion 32 thereof.

One of the benefits of using this process is that dies 84 produce very clean cut surfaces 34 and 46 with minimal bone loss. As a result, once the subsequent surgical procedure is completed, distal portion 30 can be fit back into pocket 35 with a close tolerance fit. It is appreciated that a variety of alternative configurations of die cutters can be used for selective die cutting of tibial tuberosity 20.

Figure 6:
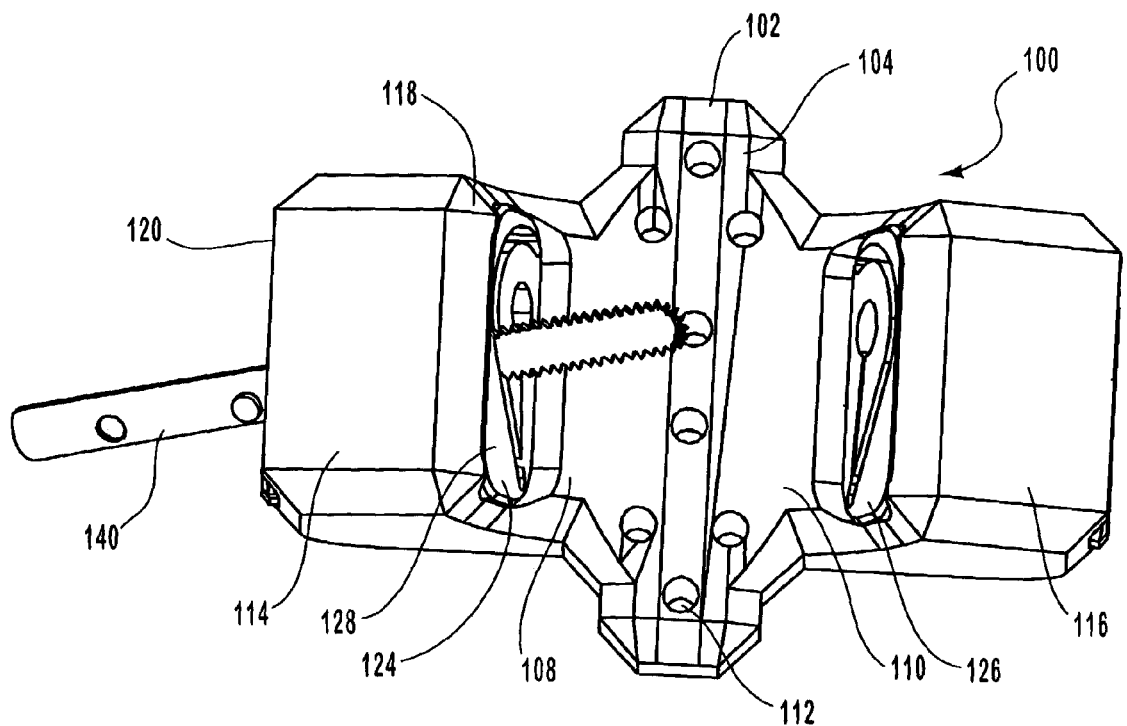
FIG. 6 is an elevated front view of a guide.
Figure 7:
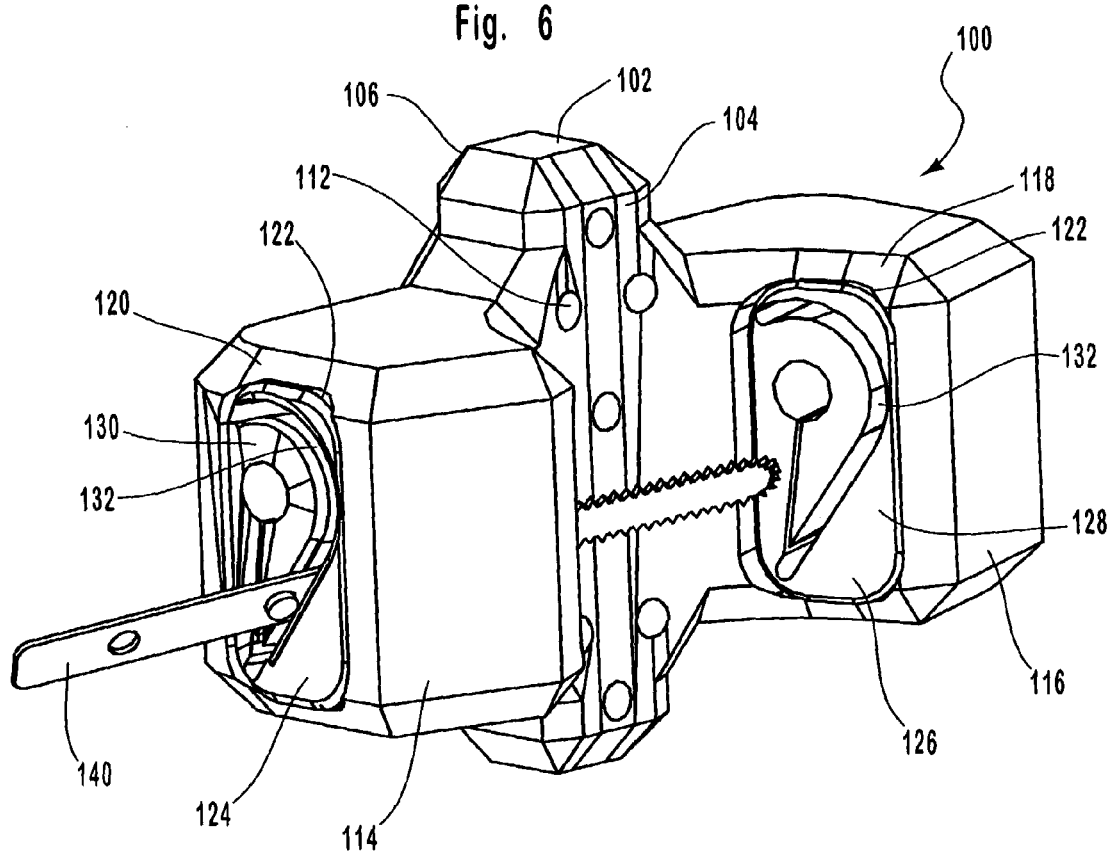
FIG. 7 is a perspective view of the guide shown in FIG. 6.
Figure 8:
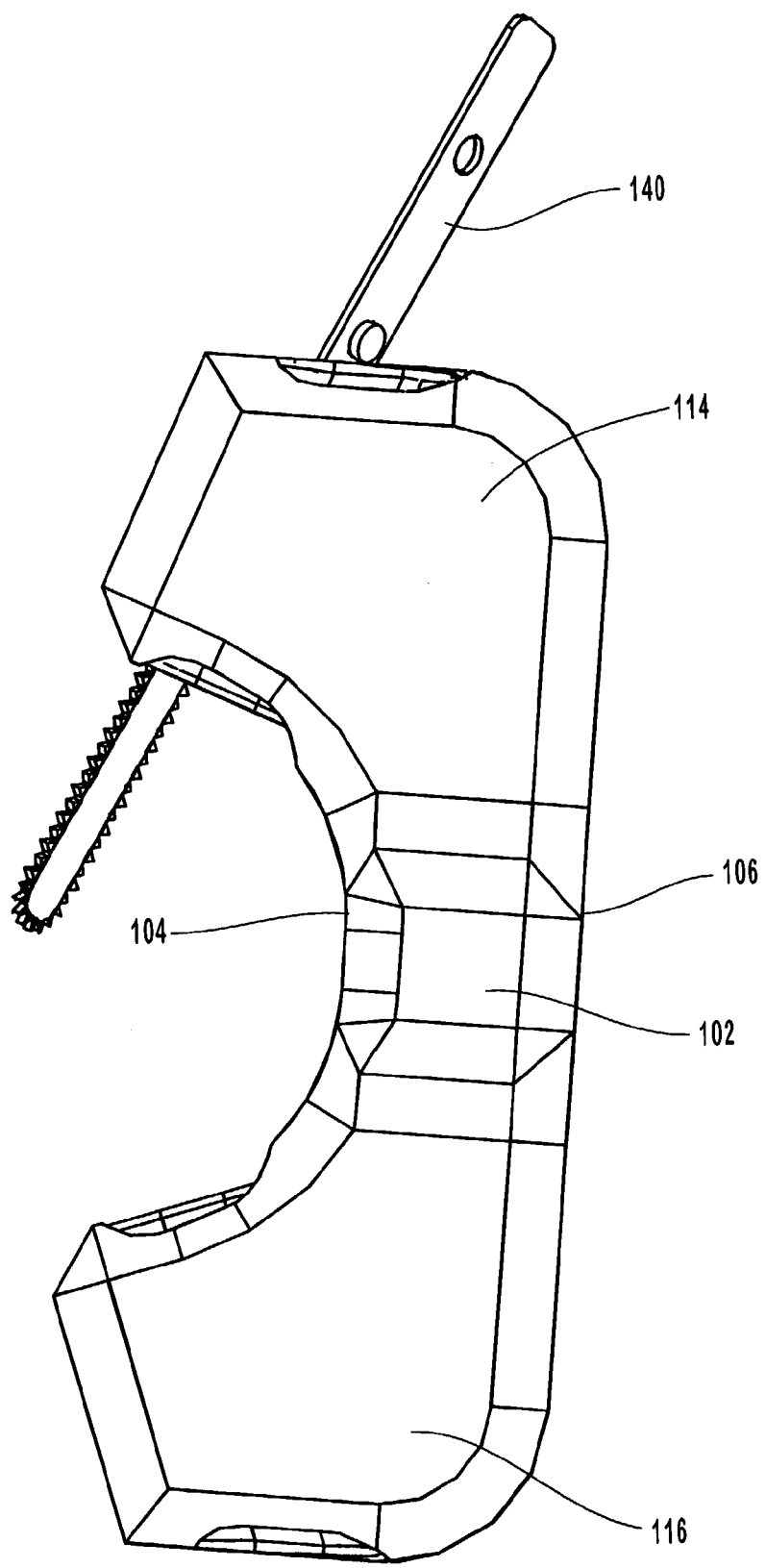
FIG. 8 is a top plan view of the guide shown in FIG. 6.

In contrast to die cutting tibial tuberosity 20, distal portion 30 of tibial tuberosity 20 can also be elevated using a saw blade. For example, depicted in FIGS. 6–8 is a guide 100. Guide 100 comprises a central plate 102 having a front face 104 and an opposing back face 106. Each of faces 104 and 106 extend between opposing sides 108 and 110. Extending between front face 104 and back face 106 are a plurality of passageways 112.

Formed on sides 108 and 110 of central plate 102 is a first side housing 114 and a second side housing 116, respectively. Each side housing 114 and 116 is formed so as to project beyond front face 104 of central plate 102. Each of side housings 114 and 116 has an inside face 118 and an opposing outside face 120. A cavity 122 extends through each of side housings 114 and 116 between faces 118 and 120. Removably disposed within cavity 122 of side housing 114 is a first template 124. A second template 126 is disposed within cavity 122 of side housing 116. Each template 124 and 126 has a substantially box-shaped configuration which includes an inside face 128 and an opposing outside face 130. Inside face 128 of templates 124 and 126 are each disposed in a corresponding plane. The planes intersect so as to form an inside angle that is substantially equal to the angle θ formed on cut surface 34.

A guide slot 132 extends through each of templates 124 and 126 between inside face 128 and outside face 130. Each guide slot 132 has a configuration complementary to the profile of cut surface 34 and extends through templates 124 and 126 at an orientation perpendicular to inside face 128.

During use, once tibial tuberosity 20 is exposed, front face 104 of central plate 102 is biased against the anterior side of tibial tuberosity 20 such that templates 124 and 126 are disposed on the lateral and medial side thereof. Guide slots 132 are aligned with distal portion 30 of tibial tuberosity 20 to be elevated. Once guide 100 is appropriately positioned, fasteners, such as screws, nails, or the like, are passed through passageways 112 and into tibia 22 so as to securely retain guide 100 to tibia 22. It is noted that passageways 112 are sloped such that the fasteners extending therethrough extend into portions of tibia 22 outside of distal portion 30 which is to be elevated.

Once guide 100 is positioned in place, a saw blade 140 is passed through guide slot 132 of template 124 from outside face 130 to inside face 128. Saw blade 140 is moved in a reciprocating manner so as to penetrate half way into tibial tuberosity 20. Once the reciprocating saw blade 140 has completed passage along guide slot 132, saw blade 140 is moved over to template 126 and passed through the guide slot 132 thereof. The process is then repeated. Once both cuttings are performed, distal portion 30 of tibial tuberosity 20 is freely removable from the remainder of tibia 22. The fasteners are then removed along with guide 100. As with die cutters 50, it is appreciated that guide 100 can come in a variety of alternative configurations.

As previously mentioned, once distal portion 30 of tibial tuberosity 20 is elevated, patellar ligament 18 is retracted proximally, thereby exposing the knee joint. Once the knee joint is exposed, any number of knee related surgical procedures, such as total or partial knee arthroplasty, can be performed. Referring back to FIG. 2, upon completion of the surgical procedure, patellar ligament 18 is secured back in place by inserting distal portion 30 of tibial tuberosity 20 back into pocket 35. As a result of undercut portion 36, distal portion 30 of tibial tuberosity 20 is self-locking within pocket 35. If desired, however, various types of conventional bone anchors can be used to further secure distal portion 30 of tibial tuberosity 20 within pocket 35.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone die cutter comprising:
   a housing having an interior surface bounding a chamber, the housing having an opening in communication with the chamber;
   a first translating arm having a proximal end and an opposing distal end, the first translating arm passing through the opening of the housing such that the proximal end is disposed within the chamber of the housing and the distal end freely extends beyond the housing;
   a second translating arm having a proximal end and an opposing distal end, the second translating arm passing through the opening of the housing such that the proximal end is disposed within the chamber of the housing and the distal end freely extends beyond the housing;
   a cutting die disposed on the distal end of each translating arm, the cutting dies having complementary configurations and being opposing facing; and
   means for selectively advancing at least one of the first and second translating arms toward the other so as to draw the cutting dies together without pivoting the first or second translating arms relative to each other.

2. A bone die cutter as recited in claim 1, wherein each die comprises a blade that terminates at a sharpened edge, the sharpened edge having a contour that corresponds substantially to the contour of the exterior surface of a vertically bisected heart design.

3. A bone die cutter as recited in claim 2, wherein the dies are positioned so that when the blades are brought together, the sharpened edges of the dies come into contact with each other substantially simultaneously along substantially the entire length of the sharpened edges.

4. A bone die cutter as recited in claim 1, wherein each die comprises an outwardly projecting blade, the dies being positioned so that the blades intersect at an angle when the blades are brought together.

5. A bone die cutter as recited in claim 1, further comprising a spacer adjustably mounted to the housing and projecting between the first and second translating arms.

6. A bone die cutter as recited in claim 5, wherein the spacer comprises a bolt in threaded engagement wit the housing.

7. A bone die cutter as recited in claim 1, wherein each translating arm has a distal end face, each cutting die being removably mounted to the distal end face of a corresponding translating arm.

8. A bone die cutter as recited in claim 7, wherein the distal end face of each translating arm is disposed in a discrete corresponding plane, the planes intersecting so as to form an inside angle in a range between about 60° to about 120°.

9. A bone die cutter as recited in claim 1, wherein the means for selectively advancing comprises a threaded shaft, the proximal end of the first and second translating arms being mounted on the shaft, selective rotation of the shaft causing at least one of the first and second translating arms to advance toward the other.

10. A bone die cutter as recited in claim 1, wherein each die comprises an outwardly projecting blade that terminates at a sharpened edge, each sharpened edge having a curved contour, and wherein the dies are positioned so that when the blades are brought together, the sharpened edges of the dies come into contact with each other substantially simultaneously along substantially the entire length of the sharpened edges.

11. A bone die cutter comprising:
    a housing comprising a first rail and a second rail;
    a first translating arm having a proximal end and an opposing distal end, the first translating arm being mounted on the housing in engagement with the first rail so that the first translating arm can selectively slide in a substantially liner path along the first rail, the distal end of the first translating arm projecting away from the housing;
    a second translating arm having a proximal end and an opposing distal end, the second translating arm being mounted on the housing in engagement with the second rail so that the second translating arm can selectively slide in a substantially linear path along the second rail, the distal end of the second translating arm projecting away from the housing;
    a first die being mounted on the distal end of the first translating arm, the first die comprising a first outwardly projecting blade;
    a second die being mounted on the distal end of the second translating arm, the second die comprising a second outwardly projecting blade, the first and second rails being configured to guide the first and second translating arms toward each other so that the first and second blades draw together without pivoting the first or second translating arms relative to each other.

12. A bone die cutter as recited in claim 11, wherein the housing comprises an interior surface bounding a chamber, the housing having an opening in communication with the chamber, the proximal end of the first and second translating arms being disposed within the chamber of the housing.

13. A bone die cutter as recited in claim 11, wherein each blade terminates at a sharpened edge, the sharpened edge having a contour that corresponds substantially to the contour of the exterior surface of a vertically bisected heart design.

14. A bone die cuter as recited in claim 13, wherein the dies are positioned so that when the blades are brought together, the sharpened edges of the dies come into contact with each other substantially simultaneously along substantially the entire length of the sharpened edges.

15. A bone die cutter as recited in claim 11, wherein each die comprises an outwardly projecting blade, the dies being positioned so that the blades intersect at an angle when the blades are brought together.

16. A bone die cutter as recited in claim 11, further comprising a spacer adjustably mounted to the housing and projecting between the first and second translating arms.

17. A bone die cutter as recited in claim 11, further comprising means for selectively advancing at least one of the first and second translating arms toward the other without pivoting the first or second translating arms relative to each other.

18. A bone die cutter as recited in claim 17, wherein the means for selectively advancing comprises a threaded shaft, the proximal end of the first and second translating arms being mounted on the threaded shaft such that selective rotation of the shaft causes at least one of the first and second translating arms to advance toward the other.

19. A bone die cutter as recited in claim 11, wherein the first and second outwardly projecting blades each terminate at a sharpened edge, each sharpened edge having a curved contour, and wherein the dies are positioned so that when the blades are brought together, the sharpened edges of the dies come into contact with each other substantially simultaneously along substantially the entire length of the sharpened edges.

* * * * *

UNITED STATES PATENT AND TRADEMARK OFFICE
CERTIFICATE OF CORRECTION

PATENT NO. : 7,112,204 B2
APPLICATION NO. : 10/360250
DATED : September 26, 2006
INVENTOR(S) : Justin et al.

It is certified that error appears in the above-identified patent and that said Letters Patent is hereby corrected as shown below:

Column 1
Line 43, change "a elevated" to --an elevated--

Column 2
Line 6, change "cad of tibia 22" to --end of tibia 22.--
Line 10, change "tat" to --that--
Line 12, change "Tn" to --In--
Line 66, change "52" to --56--

Column 4
Line 13, change "translating arm" to --translating arms--
Line 15, change "advanced" to --advance--

Column 6
Line 9, change "wit" to --with--
Line 40, change "liner path" to --linear path--

Signed and Sealed this

Twenty-first Day of August, 2007

JON W. DUDAS
*Director of the United States Patent and Trademark Office*